United States Patent
Nolan et al.

(10) Patent No.: US 9,242,107 B2
(45) Date of Patent: Jan. 26, 2016

(54) SEAL PLUG

(71) Applicant: Cardiac Pacemakers, Inc., St. Paul, MN (US)

(72) Inventors: Daragh Nolan, Via Youghal (IE); James M. English, Cahir (IE); John O'Rourke, Tip (IE); Sean Walsh, Clare (IE)

(73) Assignee: Cardiac Pacemarkers, Inc., St. Paul, MN (US)

( * ) Notice: Subject to any disclaimer, the term of this patent is extended or adjusted under 35 U.S.C. 154(b) by 0 days.

(21) Appl. No.: 14/309,866

(22) Filed: Jun. 19, 2014

(65) Prior Publication Data

US 2015/0018923 A1    Jan. 15, 2015

Related U.S. Application Data (60) Provisional application No. 61/845,535, filed on Jul. 12, 2013.

(51) Int. Cl.
| | |
|---|---|
| A61N 1/00 | (2006.01) |
| A61N 1/375 | (2006.01) |
| A61N 1/362 | (2006.01) |
| H01R 13/52 | (2006.01) |
| H01R 4/36 | (2006.01) |

(52) U.S. Cl.
CPC .............. *A61N 1/3752* (2013.01); *A61N 1/362* (2013.01); *H01R 13/5224* (2013.01); *H01R 4/36* (2013.01); *Y10T 29/49885* (2015.01)

(58) Field of Classification Search
CPC ... A61N 1/3752; A61N 1/3758; A61N 1/372; A61N 1/375
See application file for complete search history.

(56) References Cited

U.S. PATENT DOCUMENTS

| | | | |
|---|---|---|---|
| 3,822,707 | A | 7/1974 | Adducci et al. |
| 3,908,668 | A | 9/1975 | Bolduc |
| 4,072,154 | A | 2/1978 | Anderson et al. |
| 4,105,037 | A | 8/1978 | Richter et al. |
| 4,141,752 | A | 2/1979 | Shipko |
| 4,180,078 | A | 12/1979 | Anderson |
| 4,461,194 | A | 7/1984 | Moore |
| 4,479,489 | A | 10/1984 | Tucci |
| 5,000,177 | A * | 3/1991 | Hoffmann et al. ... A61N 1/3752 607/2 |
| 5,012,807 | A | 5/1991 | Stutz, Jr. |
| 5,086,773 | A | 2/1992 | Ware |
| 6,817,905 | B2 | 11/2004 | Zart et al. |
| 7,155,283 | B2 | 12/2006 | Ries et al. |
| 7,955,543 | B2 | 6/2011 | Deininger et al. |

(Continued)

*Primary Examiner* — Robert N Wieland (74) *Attorney, Agent, or Firm* — Schwegman Lundberg & Woessner, P.A.

(57) ABSTRACT

An implantable pulse generator includes a core assembly, a seal plug, and an outer layer overmolded over the core assembly adjacent the seal plug. The core assembly defines a core hole extending through the core assembly from a core interior to a core outer surface. The core hole has a hole outer portion and a hole inner portion. A first diameter of the hole outer portion is less than a second diameter of the hole inner portion. The seal plug is positioned in the core hole and has a plug outer portion aligned with the hole outer portion and a plug inner portion aligned with the hole inner portion. A third diameter of the plug outer portion is less than a fourth diameter of the plug inner portion. The outer layer leaves a top of the seal plug exposed.

20 Claims, 5 Drawing Sheets

(56) References Cited

U.S. PATENT DOCUMENTS

| | | |
|---|---|---|
| 8,103,348 B1 | 1/2012 | Coffed et al. |
| 8,315,700 B2 | 11/2012 | Citron et al. |
| 2002/0107555 A1 | 8/2002 | Rusin et al. |
| 2004/0122481 A1 | 6/2004 | Tidemand et al. |
| 2006/0015150 A1 | 1/2006 | Rusin et al. |
| 2011/0015694 A1* | 1/2011 | Alexander et al. ............ 607/36 |
| 2011/0160808 A1 | 6/2011 | Lyden et al. |
| 2012/0090161 A1 | 4/2012 | Biggs, Jr. et al. |

* cited by examiner

SEAL PLUG

CROSS-REFERENCE TO RELATED APPLICATION

This application claims priority to U.S. Provisional Application 61/845,535, filed Jul. 12, 2013, which is herein incorporated by reference in its entirety.

TECHNICAL FIELD

The present invention relates to implantable medical devices. More specifically, the invention relates to seal plugs for implantable medical devices.

BACKGROUND

Various physiological functions can be managed and/or monitored using medical devices. Many such medical devices are implantable in a human body, such as implantable cardioverter-defibrillators (ICDs) or pacemakers. Such devices typically include a housing enclosing the device and may or may not include one or more medical electrical leads that can transmit electrical signals to and/or from a sensor, electrode, or other electrical component at a distal end of the medical electrical lead. For example, such devices have been used in association with cardiac rhythm management, which can include cardiac pacing, cardiac defibrillation, and/or cardiac therapy, among other procedures.

In some such devices, the housing can isolate internal components from conductive bodily fluids after implant. Various designs for such housings are known in the art, some of which include headers with one or more seal plugs to seal holes in the headers. There exists a need for alternative designs for housings, headers, and associated seal plugs that can be used with implantable medical devices.

SUMMARY

Disclosed herein are various embodiments of medical devices and methods of attaching a seal plug to a header of a medical device.

In Example 1, a pulse generator for use in cardiac rhythm management can include a device housing containing pulse generator circuitry and a header. The header can include a core assembly, an epoxy outer layer overmolded over the core assembly, and a seal plug. The core assembly can define a terminal hole extending through the core assembly to allow insertion of a lead terminal into the core assembly and a set screw hole extending through the core assembly from a core interior to a core outer surface. The set screw hole can have a hole outer portion and a hole inner portion, wherein the core outer surface is nearer the hole outer portion than the hole inner portion. A first distance across the hole outer portion is less than a second distance across the hole inner portion. The seal plug can be positioned in the set screw hole. The seal plug can have a plug outer portion aligned with the hole outer portion and a plug inner portion aligned with the hole inner portion. A third distance across the plug outer portion can be less than a fourth distance across the plug inner portion. A top of the seal plug can be exposed by the epoxy outer layer.

In Example 2, the pulse generator according to Example 1, wherein the seal plug has a substantially frustoconical portion from the plug inner portion to the plug outer portion.

In Example 3, the pulse generator according to Example 2, wherein the epoxy outer layer covers some but not all of the substantially frustoconical portion of the seal plug.

In Example 4, the pulse generator according to any of Examples 1-3, wherein the seal plug has a deformable slit extending through the top of the seal plug through which a tool can be inserted and that is substantially closed to seal and limit fluid flow through the seal plug when the tool is removed.

In Example 5, the pulse generator according to any of Examples 1-4, wherein the core assembly comprises a core defining the hole inner portion of the set screw hole of the core assembly and a collar fixed to the core and having a collar hole defining the hole outer portion of the set screw hole of the core assembly.

In Example 6, the pulse generator according to Example 5, wherein the collar hole is substantially cylindrical and wherein the first distance is a diameter of the collar hole.

In Example 7, the pulse generator according to any of Examples 5-6, wherein the collar is connected to the core via an interference press fit.

In Example 8, the pulse generator according to any of Examples 5-7, wherein the core comprises a core rim extending from the core outer surface circumferentially around the set screw hole, wherein the collar comprises a collar rim extending toward the core, and wherein the collar rim is fixed to the core rim via an interference press fit.

In Example 9, the pulse generator according to any of Examples 1-8, and further including a set screw extending through at least a portion of the hole inner portion and covered by the seal plug.

In Example 10, the pulse generator according to Example 9, wherein the core assembly comprises an electrically insulative polymer and wherein the set screw comprises one or more electrically conductive metals.

In Example 11, an implantable pulse generator can include a core assembly defining a core hole extending through the core assembly from a core interior to a core outer surface, a seal plug positioned in the core hole, and an outer layer overmolded over the core assembly. The core hole can have a hole outer portion and a hole inner portion, wherein a first diameter of the hole outer portion is less than a second diameter of the hole inner portion. The seal plug can have a plug outer portion aligned with the hole outer portion and a plug inner portion aligned with the hole inner portion, wherein a third diameter of the plug outer portion is less than a fourth diameter of the plug inner portion. The outer layer can be overmolded over the core assembly adjacent the seal plug and can leave a top of the seal plug exposed.

In Example 12, the implantable pulse generator according to Example 11, and further including a threaded fastener extending through at least a portion of the hole inner portion and covered by the seal plug.

In Example 13, the implantable pulse generator according to Example 12, wherein the threaded fastener has a head connected to a threaded shaft, wherein the seal plug defines a plug cavity, and wherein the head is positioned at least partially in the plug cavity.

In Example 14, the implantable pulse generator according to any of Examples 11-13, wherein the seal plug has a deformable slit extending through a top of the seal plug through which a tool can be inserted and that is substantially closed to seal and limit fluid flow through the seal plug when the tool is removed.

In Example 15, the implantable pulse generator according to any of Examples 11-14, and further including a lead bore cavity receptacle positioned inside the core assembly for receiving a lead terminal of an electrical lead and a set screw oriented with respect to the lead bore cavity receptacle and configured to be tightened so as to fasten the lead terminal in the lead bore cavity receptacle.

In Example 16, the implantable pulse generator according to any of Examples 11-15, wherein an interface between the seal plug and the core assembly is substantially free of medical adhesive.

In Example 17, the implantable pulse generator according to any of Examples 11-16, wherein the implantable pulse generator comprises a cardiac resynchronization therapy device for use in cardiac rhythm management.

In Example 18, a method of manufacturing a header of a pulse generator can include forming a core assembly defining a core hole extending through the core assembly from a core interior to a core outer surface. The core hole can have a hole outer portion and a hole inner portion, and a first distance across the hole outer portion can be less than a second distance across the hole inner portion. A seal pin can be inserted in the core hole so as to extend partially outside of the core hole past the hole outer portion. Epoxy resin can be overlayed on the core outer surface adjacent to but not covering the seal pin to form a header body of the header. The seal pin can be removed from the core hole in the core assembly. A seal plug can be pushed into the core hole so that the seal plug has a plug outer portion aligned with the hole outer portion and a plug inner portion aligned with the hole inner portion. A third distance across the plug outer portion can be less than a fourth distance across the plug inner portion.

In Example 19, the method according to Example 18, wherein forming the core assembly can include molding a core having a core rim extending from the core outer surface circumferentially around the core hole and pressing a collar having a collar rim onto the core rim so as to be attached in an interference fit.

In Example 20, the method according to any of Examples 18-19, wherein the seal pin comprises an acetal homopolymer that repels the epoxy resin when the epoxy resin is overlayed on the core outer surface.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
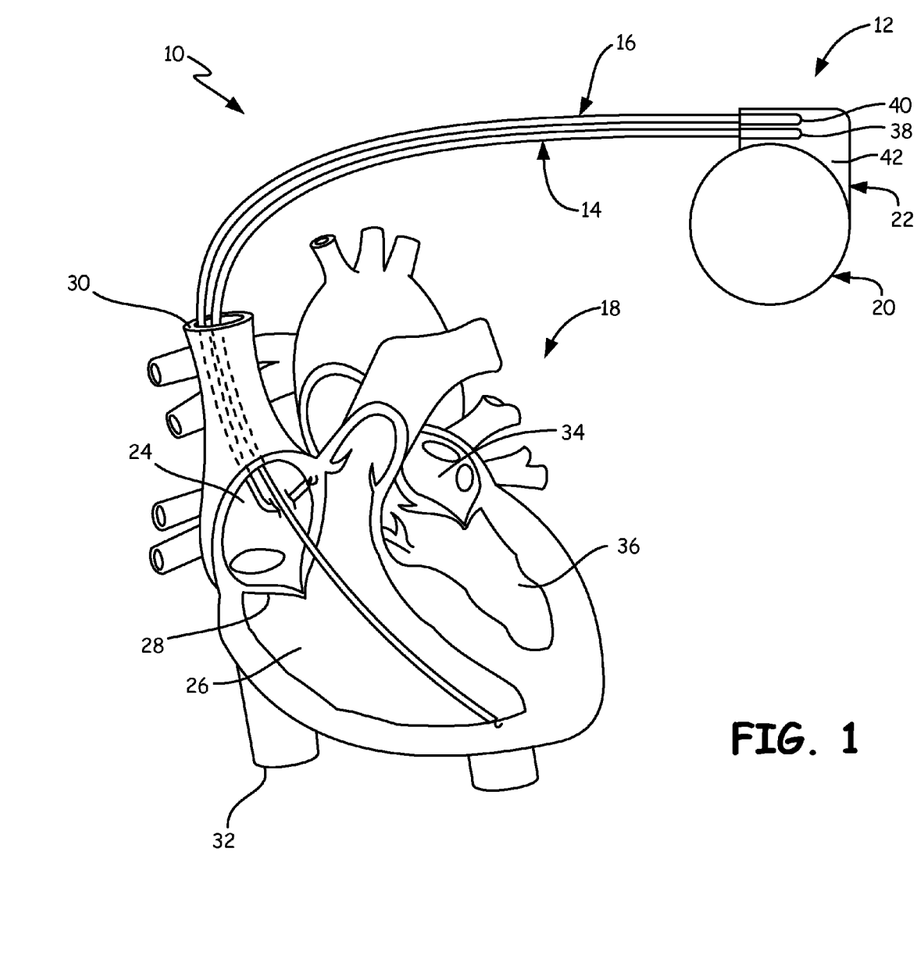
FIG. 1 is a schematic view of a cardiac rhythm management (CRM) system according to one embodiment of the present invention.

FIG. 1 is a schematic view of a cardiac rhythm management (CRM) system 10 according to one embodiment. As shown in FIG. 1, the CRM system 10 includes a pulse generator 12 coupled to a plurality of leads 14 and 16 deployed in a patient's heart 18. The pulse generator 12 includes a housing 20 and a header 22 mounted on the housing 20. As further shown in FIG. 1, the heart 18 includes a right atrium 24 and a right ventricle 26 separated by a tricuspid valve 28. During normal operation of the heart 18, deoxygenated blood is fed into the right atrium 24 through the superior vena cava 30 and the inferior vena cava 32. As further shown, the heart 18 includes a left atrium 34, which receives oxygenated blood from the lungs, and a left ventricle 36, which pumps the oxygenated blood to the body.

The leads 14 and 16 are medical electrical leads that operate to convey electrical signals and stimuli between the heart 18 and the pulse generator 12. The header 22 of the pulse generator 12 is an output terminal header with cores 38 and 40 substantially encapsulated in a header body 42. The cores 38 and 40 are output terminal cores for receiving proximal ends of the leads 14 and 16, respectively. In the illustrated embodiment, a distal end of the lead 14 is implanted in the right ventricle 26, and a distal end of the lead 16 is implanted in the right atrium 24. In other embodiments, the CRM system 10 may include additional leads, e.g., a lead extending into a coronary vein for stimulating the left ventricle in a bi-ventricular pacing or cardiac resynchronization therapy (CRT) system. As shown, the leads 14 and 16 enter the superior vena cava 30, and are implanted in the right ventricle 26 and right atrium 24, respectively.

The pulse generator 12 can be implanted subcutaneously within an implantation location or pocket in the patient's chest or abdomen. The pulse generator 12 can be an implantable medical device known in the art, or later developed, for delivering an electrical therapeutic stimulus to the patient. In various embodiments, the pulse generator 12 can be a neurostimulation device, a pacemaker, a CRT device, an implantable cardiac defibrillator, and/or can include both pacing, CRT and/or defibrillation capabilities (e.g., a CRT-D device).

In some embodiments the CRM system 10 can be configured to stimulate cardiac tissue and/or sense certain physiological attributes of the heart. However, in discussing embodiments of the present disclosure, reference is made primarily to stimulating body tissues. Those of ordinary skill in the art will recognize that some or all of the configurations can also be used to receive electrical signals from the body.

Figure 2A:
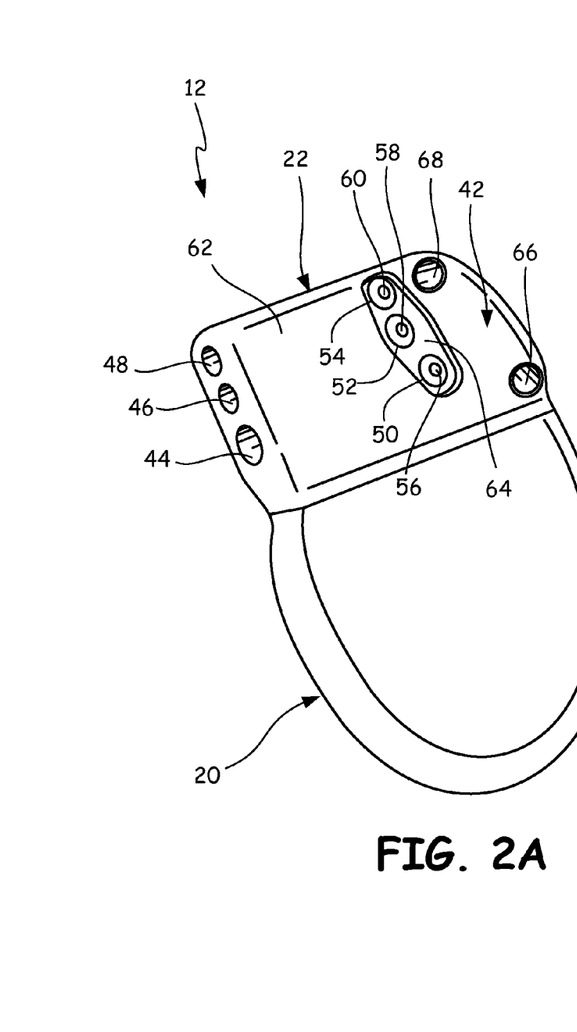
FIG. 2A is a perspective view of one embodiment of a pulse generator for use in the CRM system of FIG. 1, with an opaque header body.

FIG. 2A is a perspective view of the pulse generator 12 with the header 22 having an opaque header body 42. The header 22 has a plurality of receptacles 44, 46, and 48 in the header body 42. The receptacles 44, 46, and 48 are terminal holes that allow lead terminal pins of leads, such as the leads 14 and 16 (shown in FIG. 1) to be inserted into cores, such as the cores 38 and 40 (shown in FIG. 1). Because the header body 42 is opaque, the cores 38 and 40 are not visible in FIG. 2A.

The header 22 also has a plurality of holes 50, 52, and 54, which are set screw holes that allow access to set screws (not shown in FIG. 2A) that can be tightened to fasten the lead terminals of the leads 14 and 16 in the cores 38 and 40. Plugs 56, 58, and 60 are seal plugs that are inserted into and seal the holes 50, 52, and 54, respectively.

In the illustrated embodiment, the header body 42 has an outer surface 62 and an indented surface 64 sunken below the outer surface 62. The outer surface 62 and the indented surface 64 both face substantially outward from the header body 42. The indented surface 64 surrounds the holes 50, 52, and 54. The plugs 56, 58, and 60 are positioned in the holes 50, 52, and 54 so as to extend above the indented surface 64 but, in the illustrated embodiment, do not extend substantially above the outer surface 62. The header body 42 can also have one or more fastener holes 66 and 68 that can be used for attaching sutures or other fasteners to hold the pulse generator 12 in place when implanted in a human body.

Figure 2B:
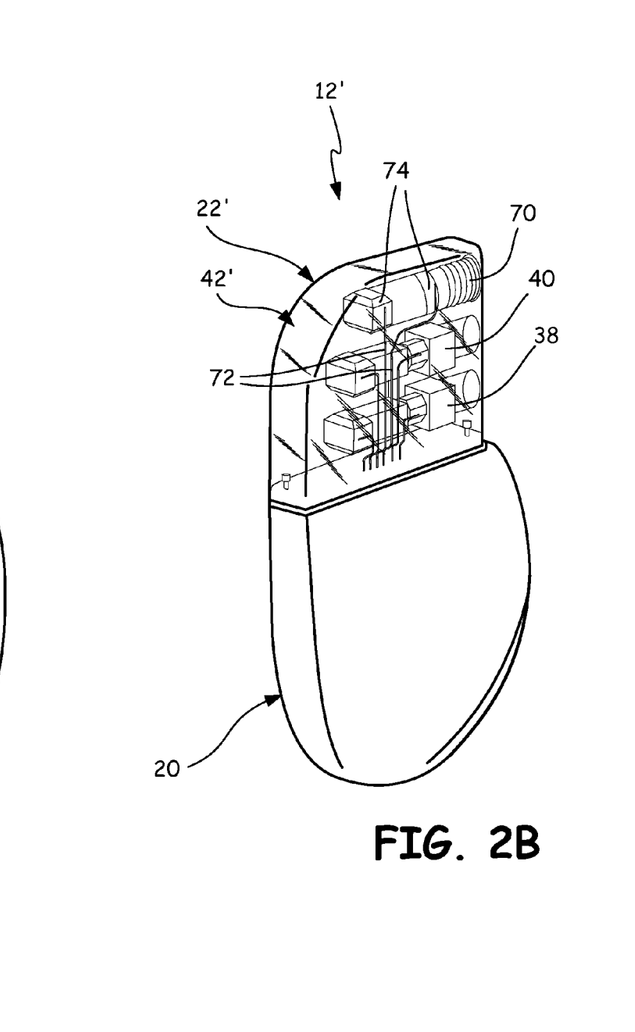
FIG. 2B is a perspective view of another embodiment of a pulse generator for use in the CRM system of FIG. 1, with a transparent header body.

FIG. 2B is another perspective view of a pulse generator 12', which is similar to the pulse generator 12 (shown in FIG. 2A) except that the pulse generator 12' has a header body 42' that is transparent. Because the header body 42' is transparent, the cores 38 and 40, as well as another core 70, are visible. A plurality of electrical leads 72 connect pulse generator circuitry (not shown) within the housing 20 to electrical contacts 74 on the cores 38, 40, and 70. Thus, the pulse generator 12' can transmit electrical signals to and from leads (such as the leads 14 and 16, shown in FIG. 1) connected to the header 22'.

Although the header 22' is shown in FIG. 2B as having three cores (the cores 38, 40, and 70) for connecting to three leads (not shown), the header 22' can have one, two, or more than three cores as suitable for a particular application. The cores 38, 40, and 70 are illustrated as three distinct cores. Alternatively, the cores 38, 40, and 72 can be combined as a single core having multiple receptacles (such as the receptacles 44, 46, and 48 as shown in FIG. 2A).

Figure 3:
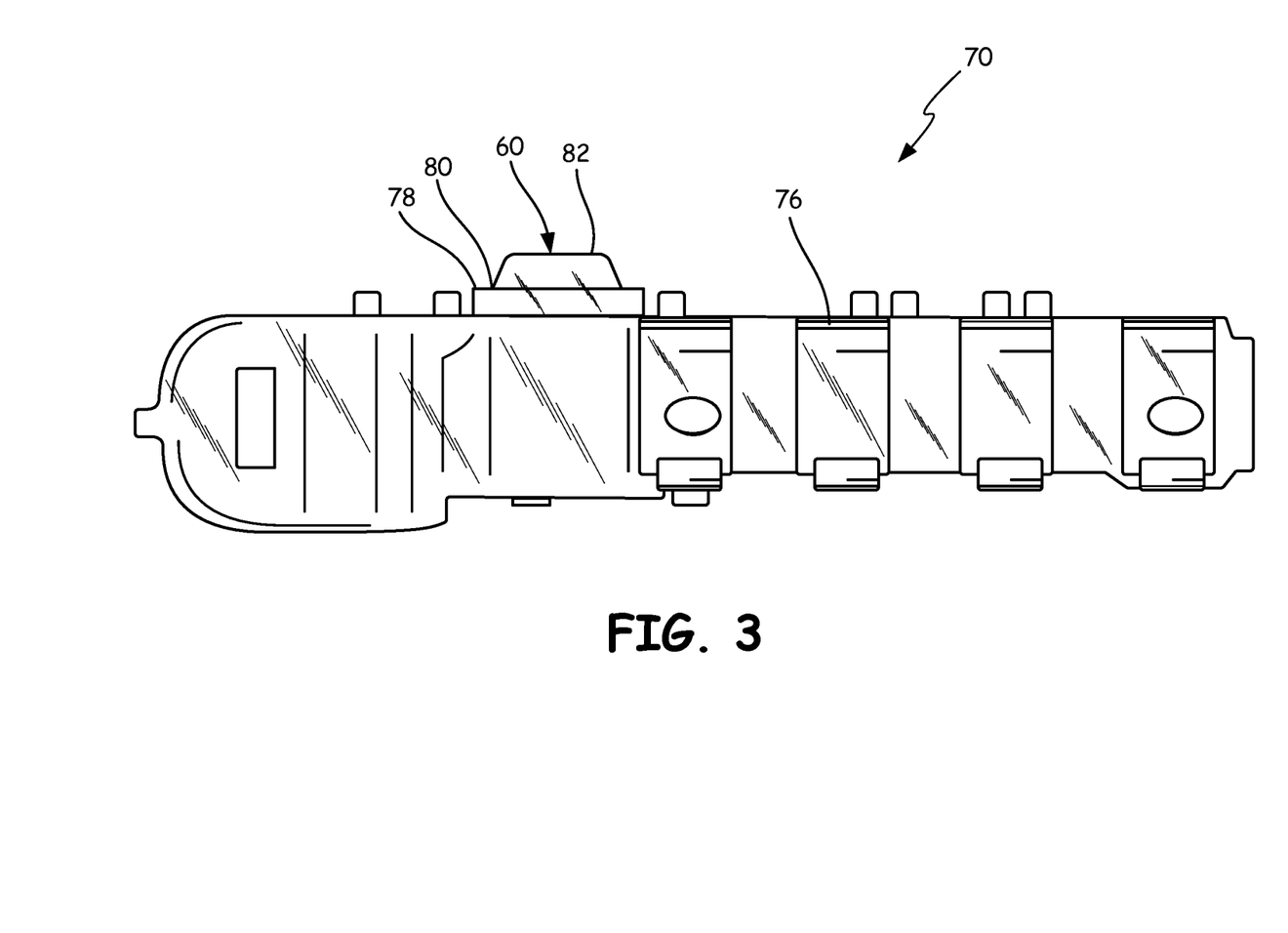
FIG. 3 is a side view of an output terminal core of the pulse generator.

FIG. 3 is a side view of the core 70. The core 70 has a core outer surface 76 and a core rim 78 extending from the core outer surface 76. The core rim 78 extends circumferentially around a core hole 80, which forms part of the hole 54 (shown in FIG. 2A). The plug 60 is positioned partially inside the core hole 80, with a top 82 extending above the core hole 80. The core 70 can be made of an engineered thermoplastic polyurethane (ETPU) material or other suitable polymer.

Figure 4:
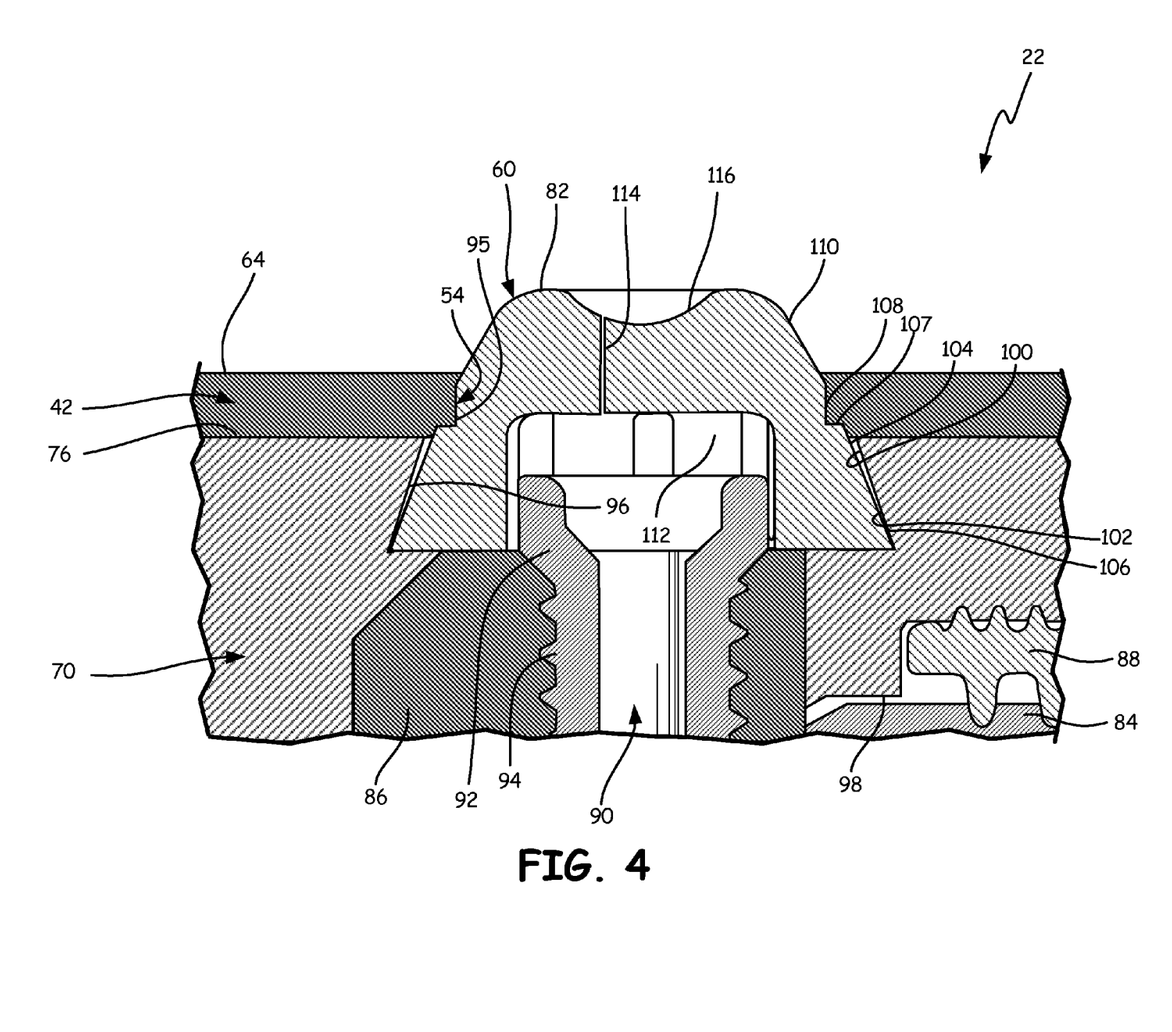
FIG. 4 is a sectional view of a portion of one embodiment of the epoxy header body and the output terminal core.

FIG. 4 is a sectional view of the header 22, showing the header body 42, the core 70, and the plug 60. The core 70 contains a lead bore cavity 84 and a tip block 86. An inner seal 88 provides a substantially fluid tight seal between the core 70 and the lead bore cavity 84. A threaded fastener 90 has a head 92 connected to a threaded shaft 94. The threaded fastener 90 is a set screw threadedly engaged with the tip block 86. The lead bore cavity 84 is a receptacle for receiving a lead terminal on a proximal end of an electrical lead (such as the leads 14 and 16 of FIG. 1) in the lead bore cavity 84. The threaded fastener 90 can be tightened so as to fasten the lead terminal in the lead bore cavity 84. The threaded fastener 90, the tip block 86, and the lead bore cavity 84 can be made of electrically conductive metal so as to conduct signals to and from the electrical lead.

The hole 54 is a set screw hole that extends through the header 22. The hole 54 includes a header body hole 95 extending through and defined by the header body 42 and a core hole 96 extending through and defined by the core 70. The core hole 96 extends from a core interior 98 to the core outer surface 76. The core hole 96 has a hole outer portion 100 and a hole inner portion 102. The core outer surface 76 is nearer the hole outer portion 100 than the hole inner portion 102. A distance across the hole outer portion 100 is less than a distance across the hole inner portion 102. In the illustrated embodiment, the core hole 96 tapers from the hole inner portion 102 to the hole outer portion 100.

The plug 60 is positioned in the core hole 96. The plug 60 has a plug outer portion 104 aligned with the hole outer portion 100 and has a plug inner portion 106 aligned with the hole inner portion 102. A distance across the plug outer portion 104 is substantially equal to the distance across the hole outer portion 100. A distance across the plug inner portion 106 is substantially equal to the distance across the hole inner portion 102. Thus, the distance across the plug outer portion 104 is less than the distance across the plug inner portion 106. In the illustrated embodiment, the plug 60 tapers from the plug inner portion 106 to the plug outer portion 104. The plug 60 has a substantially frustoconical shape between the plug inner portion 106 and the plug outer portion 104. Thus, the distance across the plug outer portion 104 is a diameter of the plug outer portion 104 and the distance across the plug inner portion 106 is a diameter of the plug inner portion 106.

In the illustrated embodiment, the plug 60 includes a radially inward step 107 adjacent the plug outer portion 104, and a cylindrical portion 108 adjacent the step 107. Another frustoconical portion 110 is positioned between the cylindrical portion 108 and the top 82 of the plug 60. The header body hole 95 of the header body 42 is aligned with the step 107, the cylindrical portion 108, and part of the frustoconical portion 110. The header body 42 is an epoxy outer layer overmolded over the core 70 that leaves the top 82 of the plug 60 exposed.

The plug 60 defines a plug cavity 112 opposite of the top 82 of the plug 60. A slit 114 extends from a concave indentation 116 on the top 82 of the plug 60, through the top 82 of the plug 60, to the plug cavity 112. The head 92 of the threaded fastener 90 is positioned at least partially in the plug cavity 112. Under normal operation, the slit 114 is substantially closed to seal and limit fluid flow through the plug 60. The slit 114 is deformable, allowing a tool (not shown) to be inserted through the slit 114 into the head 92 of the threaded fastener 90 to turn the threaded fastener. When the tool is removed, the slit 114 can resiliently return to its original, sealed configuration. The plug 60 can be made of a resilient polymer material suitable for sealing the hole 54.

The shapes of the plug 60 and the core hole 96 can help retain the plug 60 in the core hole 96. Because the distance across the plug outer portion 104 (and across the hole outer portion 100) is smaller than the distance across the plug inner portion 106 (and the hole inner portion 102), the plug 60 can be prevented from falling out of the core hole 96 during normal operation of the pulse generator 12 (shown in FIG. 1). The plug 60 can be retained in the core hole 96 without using medical adhesive. In the illustrated embodiment, the header body hole 95 of the header body 42 is sized and shaped to further retain the plug 60 in the core hole 96. In alternative embodiments, the plug 60 can be retained in the core hole 96 due to the shapes of the plug 60 and the core hole 96 without any retaining force provided by the epoxy layer that forms the header body 42.

The header 22 can be formed by first premolding the core 70. The core 70 can be molded in the shape substantially as illustrated, including the core hole 96. Then a seal pin (not shown) can be inserted into the core hole 96, extending partially outside the core hole 96, to temporarily seal the core hole 96. The seal pin can be made of polyoxymethylene (POM), also known as acetal, which can repel the epoxy resin when the epoxy resin is overlayed on the core outer surface 76. In one embodiment, the seal pin can be made of a POM homopolymer such as a POM homopolymer resin sold by E. I. DuPont de Nemours and Company of Wilmington, Del. USA under the trademark Delrin®. In other embodiments, the seal pin can be made of a POM copolymer.

Epoxy resin can then be overlayed on the core outer surface 76 to form the header body 42. The epoxy resin can be overlayed adjacent to but not covering the seal pin. Once the epoxy resin is hardened, the seal pin can then be removed from the core hole 96. Then, the seal plug 60 can be pushed through the header body hole 95 and into the core hole 96, such that the plug outer portion 104 is aligned with the hole outer portion 100 and the plug inner portion 106 is aligned with the hole inner portion 102, substantially as illustrated in FIG. 4.

Figure 5:
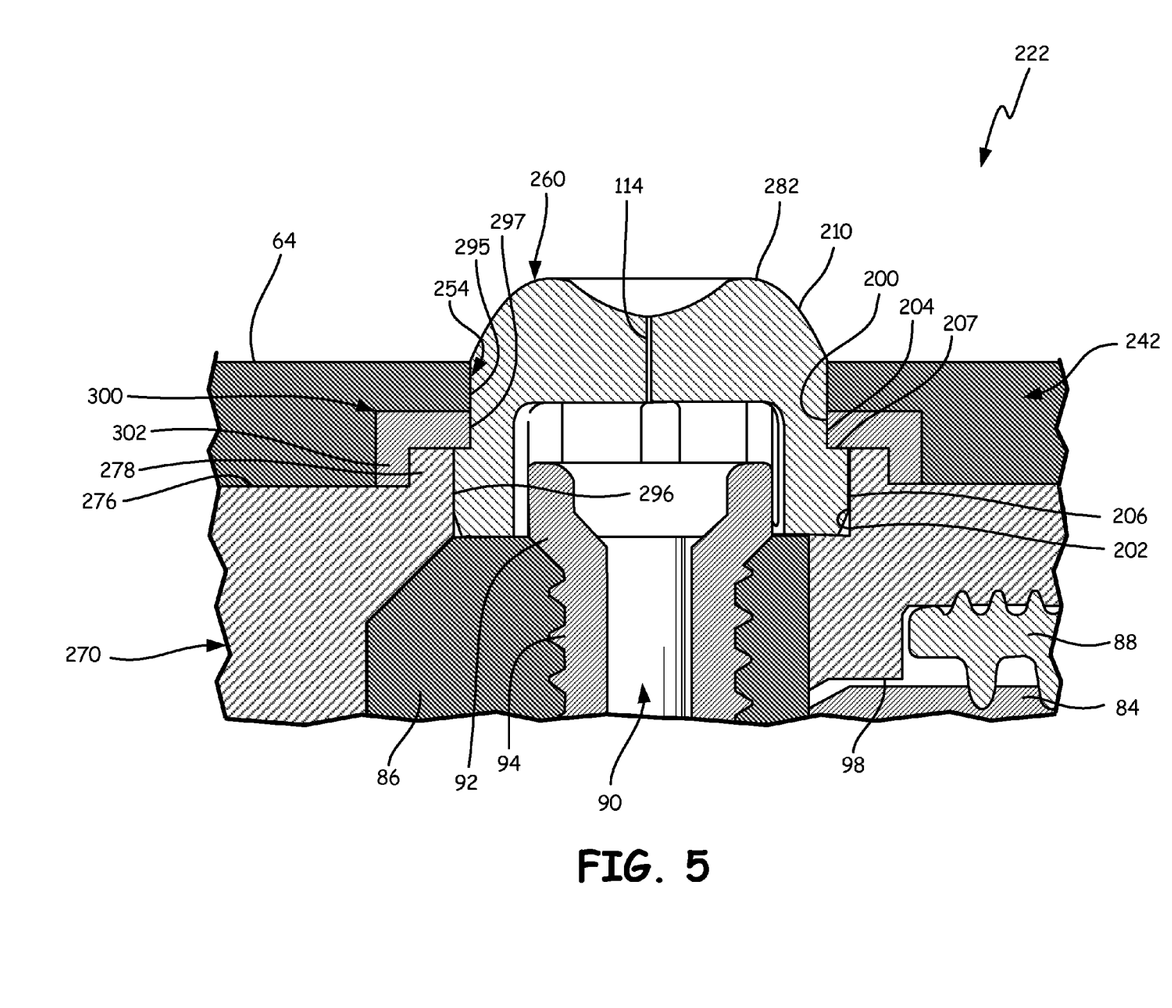
FIG. 5 is a sectional view of a portion of another embodiment of the epoxy header body and the output terminal core.

FIG. 5 is a sectional view of a header 222, with a header body 242, a core 270, and a plug 260. The header 222 is similar to the header 22 (shown in FIG. 4), except that the header 222 has a hole 254 that is shaped and configured differently than hole 54 (shown in FIG. 4). The hole 254 includes a header body hole 295 extending through and defined by the header body 242, a core hole 296 extending through and defined by the core 270, and a collar hole 297 extending through and defined by a collar 300.

The collar 300 is fixed to the core 270 such that the collar hole 297 is substantially aligned with the core hole 296. The core 270 has a core rim 278 extending from a core outer surface 276 circumferentially around the core hole 296 and toward the collar 300. The collar 300 has a collar rim 302 extending circumferentially around the collar hole 297 and toward the core 270. The collar rim 302 is positioned around the core rim 278 and is fixed to the core rim 278 via an interference press fit. The core 270 and the collar 300 combine to form a core assembly. In various embodiments, the core assembly can include more or fewer components. For example, in the embodiment of FIG. 4, the core assembly is formed without the collar 300.

In the embodiment of FIG. 5, the collar hole 297 defines a hole outer portion 200 of the hole 254, and the core hole 296 defines a hole inner portion 202 of the hole 254. A distance across the hole outer portion 200 is less than a distance across the hole inner portion 202. In the illustrated embodiment, the collar hole 297 is substantially cylindrical such that the distance across the hole outer portion 200 is a diameter of the collar hole 297. Similarly, the core hole 296 is also substantially cylindrical such that the distance across the hole inner portion 202 is a diameter of the core hole 296. Thus, the diameter of the collar hole 297 is smaller than the diameter of the core hole 296.

The plug 260 is positioned in the hole 254. The plug 260 has a plug outer portion 204 aligned with the hole outer portion 200 and has a plug inner portion 206 aligned with the hole inner portion 202. A distance across the plug outer portion 204 is substantially equal to the distance across the hole outer portion 200. A distance across the plug inner portion 206 is substantially equal to the distance across the hole inner portion 202. Thus, the distance across the plug outer portion 204 is less than the distance across the plug inner portion 206. In the illustrated embodiment, a radial step 207 creates a transition between the plug outer portion 204 and the plug inner portion 206. A frustoconical portion 210 is positioned between the plug outer portion 204 and the top 282 of the plug 260. The header body hole 295 of the header body 242 is aligned with part of the plug outer portion 204 and part of the frustoconical portion 210.

The shapes of the plug 260 and the hole 254 can help retain the plug 260 in the hole 254. Because the distance across the plug outer portion 204 (and across the hole outer portion 200) is smaller than the distance across the plug inner portion 206 (and the hole inner portion 202), the plug 260 can be prevented from falling out of the hole 254 during normal operation of the pulse generator 12 (shown in FIG. 1). The collar 300 holds the plug 260 at the radial step 207. The plug 260 can be retained in the hole 254 without using medical adhesive. In the illustrated embodiment, the header body hole 295 of the header body 242 is sized and shaped to further retain the plug 260 in the hole 254. In alternative embodiments, the plug 260 can be retained in the hole 254 due to the shapes of the plug 260 and the collar hole 297 without any retaining force provided by the header body 242.

The header 222 can be formed by first premolding the core 270. The core 270 can be molded in the shape substantially as illustrated, including the core hole 296 and the core rim 278. The collar 300 can be premolded separately from the core 270 and formed in the shape substantially as illustrated, including the collar hole 297 and the collar rim 302. Then the collar 300 can be pressed on the core rim 278 so as to be attached in an interference fit, thus forming the core assembly. Then a seal pin (not shown) can be inserted into the core hole 296 and collar hole 297, extending partially outside the core hole 296 and collar hole 297, to temporarily seal the core hole 296 and collar hole 297. Epoxy resin can then be overlayed on the core outer surface 276 and the collar 300 to form the header body 242. The epoxy resin can be overlayed adjacent to but not covering the seal pin. Once the epoxy resin is hardened, the seal pin can then be removed from the core hole 296 and the collar hole 297. Then, the seal plug 260 can be pushed through the header body hole 295 and into the core hole 296 and the collar hole 297, such that the plug outer portion 204 is aligned with the hole outer portion 200 and the plug inner portion 206 is aligned with the hole inner portion 202, substantially as illustrated in FIG. 5.

Thus, the plugs 60 and 260 can be pushed into the holes 54 and 254, respectively, to substantially seal the holes 54 and 254 from conductive bodily fluids, and thus electrically isolate the threaded fastener 90 and the tip block 86. The plugs 60 and 260 can be retained in the holes 54 and 254 without using medical adhesive. The plugs 60 and 260 can be retained in the core holes 96 and 296 (with or without use of the collar 300) without relying on any retaining function from the header bodies 42 and 242, which can thus increase reliability. The total assembly time of the header 22 can thus be reduced, as well as the overall cost.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A pulse generator for use in cardiac rhythm management, the pulse generator comprising:
    a device housing containing pulse generator circuitry; and
    a header comprising:
        a core assembly defining:
            a terminal hole extending through the core assembly to allow insertion of a lead terminal into the core assembly; and
            a set screw hole extending through the core assembly from a core interior to a core outer surface, the set screw hole having a hole outer portion and a hole inner portion, wherein the core outer surface is nearer the hole outer portion than the hole inner portion, and wherein a first distance across the hole outer portion is less than a second distance across the hole inner portion;
        an epoxy outer layer overmolded over the core assembly; and a seal plug positioned in the set screw hole, wherein the seal plug has a plug outer portion aligned with the hole outer portion and a plug inner portion aligned with the hole inner portion, wherein a third distance across the plug outer portion is less than a fourth distance across the plug inner portion, and wherein a top of the seal plug is exposed by the epoxy outer layer.

2. The pulse generator of claim 1, wherein the seal plug has a substantially frustoconical portion from the plug inner portion to the plug outer portion.

3. The pulse generator of claim 2, wherein the epoxy outer layer covers some but not all of the substantially frustoconical portion of the seal plug.

4. The pulse generator of claim 1, wherein the seal plug has a deformable slit extending through the top of the seal plug through which a tool can be inserted and that is substantially closed to seal and limit fluid flow through the seal plug when the tool is removed.

5. The pulse generator of claim 1, wherein the core assembly comprises:
  a core defining the hole inner portion of the set screw hole of the core assembly; and
  a collar fixed to the core and having a collar hole defining the hole outer portion of the set screw hole of the core assembly.

6. The pulse generator of claim 5, wherein the collar hole is substantially cylindrical and wherein the first distance is a diameter of the collar hole.

7. The pulse generator of claim 5, wherein the collar is connected to the core via an interference press fit.

8. The pulse generator of claim 5, wherein the core comprises a core rim extending from the core outer surface circumferentially around the set screw hole, wherein the collar comprises a collar rim extending toward the core, and wherein the collar rim is fixed to the core rim via an interference press fit.

9. The pulse generator of claim 1, and further comprising:
  a set screw extending through at least a portion of the hole inner portion and covered by the seal plug.

10. The pulse generator of claim 9, wherein the core assembly comprises an electrically insulative polymer and wherein the set screw comprises one or more electrically conductive metals.

11. An implantable pulse generator comprising:
  a core assembly defining a core hole extending through the core assembly from a core interior to a core outer surface, the core hole having a hole outer portion and a hole inner portion, wherein a first diameter of the hole outer portion is less than a second diameter of the hole inner portion;
  a seal plug positioned in the core hole, wherein the seal plug has a plug outer portion aligned with the hole outer portion and a plug inner portion aligned with the hole inner portion, wherein a third diameter of the plug outer portion is less than a fourth diameter of the plug inner portion; and
  an outer layer overmolded over the core assembly adjacent the seal plug and leaving a top of the seal plug exposed.

12. The implantable pulse generator of claim 11, and further comprising:
  a threaded fastener extending through at least a portion of the hole inner portion and covered by the seal plug.

13. The implantable pulse generator of claim 12, wherein the threaded fastener has a head connected to a threaded shaft, wherein the seal plug defines a plug cavity, and wherein the head is positioned at least partially in the plug cavity.

14. The implantable pulse generator of claim 13, wherein the seal plug has a deformable slit extending through a top of the seal plug through which a tool can be inserted and that is substantially closed to seal and limit fluid flow through the seal plug when the tool is removed.

15. The implantable pulse generator of claim 11, and further comprising:
  a lead bore cavity receptacle positioned inside the core assembly for receiving a lead terminal of an electrical lead; and
  a set screw oriented with respect to the lead bore cavity receptacle and configured to be tightened so as to fasten the lead terminal in the lead bore cavity receptacle.

16. The implantable pulse generator of claim 11, wherein an interface between the seal plug and the core assembly is substantially free of medical adhesive.

17. The implantable pulse generator of claim 11, wherein the implantable pulse generator comprises a cardiac resynchronization therapy device for use in cardiac rhythm management.

18. A method of manufacturing a header of a pulse generator, the method comprising:
  forming a core assembly defining a core hole extending through the core assembly from a core interior to a core outer surface, the core hole having a hole outer portion and a hole inner portion, and wherein a first distance across the hole outer portion is less than a second distance across the hole inner portion;
  inserting a seal pin in the core hole so as to extend partially outside of the core hole past the hole outer portion;
  overlaying epoxy resin on the core outer surface adjacent to but not covering the seal pin to form a header body of the header;
  removing the seal pin from the core hole in the core assembly; and
  pushing a seal plug into the core hole so that the seal plug has a plug outer portion aligned with the hole outer portion and a plug inner portion aligned with the hole inner portion, wherein a third distance across the plug outer portion is less than a fourth distance across the plug inner portion.

19. The method of claim 18, wherein forming the core assembly comprises:
  molding a core having a core rim extending from the core outer surface circumferentially around the core hole; and
  pressing a collar having a collar rim onto the core rim so as to be attached in an interference fit.

20. The method of claim 18, wherein the seal pin comprises an acetal homopolymer, and wherein the acetal homopolymer repels the epoxy resin when the epoxy resin is overlayed on the core outer surface.

* * * * *